United States Patent [19]

Kolehmainen et al.

[11] 4,349,510

[45] Sep. 14, 1982

[54] METHOD AND APPARATUS FOR MEASUREMENT OF SAMPLES BY LUMINESCENCE

[76] Inventors: Seppo Kolehmainen, P.O. Box 2805, Titusville, Fla. 32780; Veikko Tarkkanen, Krijgersberglaan 25, 6371 CA Schaesberg, Netherlands

[21] Appl. No.: 171,323

[22] Filed: Jul. 23, 1980
(Under 37 CFR 1.47)

[30] Foreign Application Priority Data

Jul. 24, 1979 [GB] United Kingdom ............... 7925713

[51] Int. Cl.³ ..................... G01N 33/52; G01N 35/02
[52] U.S. Cl. ..................................... 422/66; 356/244; 422/102; 422/52; 435/808
[58] Field of Search ............... 422/52, 65, 66, 102, 422/104; 435/805, 300, 808; 250/227; 356/244

[56] References Cited

U.S. PATENT DOCUMENTS

| | | | |
|---|---|---|---|
| 3,356,462 | 12/1967 | Cooke et al. | 422/102 |
| 3,620,678 | 11/1971 | Guigan | 422/66 |
| 3,676,080 | 7/1972 | Richterich | 422/66 |
| 4,013,418 | 3/1977 | Plakas | 422/52 |
| 4,240,751 | 12/1980 | Linneck et al. | 250/227 |
| 4,245,052 | 7/1981 | Land | 422/102 |
| 4,263,256 | 4/1981 | Morle | 422/66 |
| 4,264,560 | 4/1981 | Natelson | 422/66 |
| 4,291,230 | 9/1981 | Heiss | 356/244 |

*Primary Examiner*—Michael S. Marcus

[57] ABSTRACT

The invention relates to automatic transportation, processing and measurement of chemiluminescence and bioluminescence in discrete samples contained in depressions on a light-reflecting tape. The tape may have either one row of sample wells for measurement of luminescence with a single light detector, or consecutive rows of 2-10 samples or more for simultaneous measurement of luminescence with a multi-detector array having an equal number of individual detectors as there are samples in one row. Processing and measurement of up to 500 samples per hour with a single detector and up to several thousands of samples per hour with the multi-detector system is possible.

21 Claims, 4 Drawing Figures

METHOD AND APPARATUS FOR MEASUREMENT OF SAMPLES BY LUMINESCENCE

BACKGROUND OF THE INVENTION

The present invention relates to the automatic transportation, processing and measurement of the chemiluminescence and bioluminescence of substances.

Bioluminescence and chemiluminescence have been applied for various types of measurements of substances (Gorus, F. and E. Schram. Clin. Chem. 25: 512–5, 1979), viability of cells (Tarkkanen, P., R. Driesch and H. Greiling. Fresenius Z. Anal. Chem. 290: 180–181, 1978) and as a means for the quantification of antigen–antibody complexes (Velan, B. and M. Halmann. Immonu Chemistry 15:331–33,1978).

Normally the bio- and chemiluminescence measurements are carried out in manually operated instruments, although flow-through systems have been applied for purposes of automation. A segmented flow-through system applies air bubbles to separate samples and to mix samples with reagents (Johnston, H.H., C.J. Mitchell and G.D.W. Curtis, pp.210–214, In Rapid Methods and Automation in Microbiology (H.H. Johnston and S.W.B. Newsom, Eds.); Learned Information (Europe) Ltd., Oxford, 1976), while in so-called Flow Injection Analysis (FIA) the homogeneous samples move in capillaries. Certain nonhomogenous samples, such as cell samples, biological fluids (blood, urine, milk) are not easily applicable to a flow-through system because of problems associated with precipitation of cells, proteins, fat globules and other particles in the tubes and capillaries. Therefore, the measurement of such samples is more reliable when the samples are handled discretely in individual containers through all steps in the analyzing procedure.

Automatic luminescence measurement of discrete samples has been possible with a liquid scintillation counter by applying special modification to provide automatic reagent dispensing (see Hammerstedt, R.H. Anal. Biochem. 52:449–455, 1973) or in an instrument applying a light-transparent filter for carrying samples and reagents.

Liquid scintillation counters (LSC) are expensive, voluminous and not-optimal for luminescence measurements. The most important draw-backs of a liquid scintillation counter are that the sample size is large (from 2–10 ml), dynamic range is only 2–3 decades and there is a 20 second delay before the sample goes from the transport mechanism ot the measuring position. Furthermore, these counters are difficult to apply for automatic sample processing as automatic injection of reagents and incubation at a given temperature cannot be accomplished without significant changes in the original construction.

An instrument using a light-transparent filter disclosed in U.S. Pat. No. 3,940,250 is meant only for samples to be filtered and its use is limited to small sample and reagent volumes only. Furthermore, it can be used only for one analysis at a time.

It is, therefore, an object of the present invention to provide a method and apparatus for measuring of samples by luminescence which will overcome the above disadvantages.

BRIEF SUMMARY OF THE INVENTION

According to the invention discrete samples contained in depressions in a light-reflecting tape or foil are automatically transported, processed and their chemiluminescence and/or bioluminescence measured.

BRIEF DESCRIPTION OF THE DRAWINGS

The invention is illustrated by way of example in the attached drawings, in which.

DETAILED DESCRIPTION OF PREFERRED EMBODIMENTS

Figure 1:
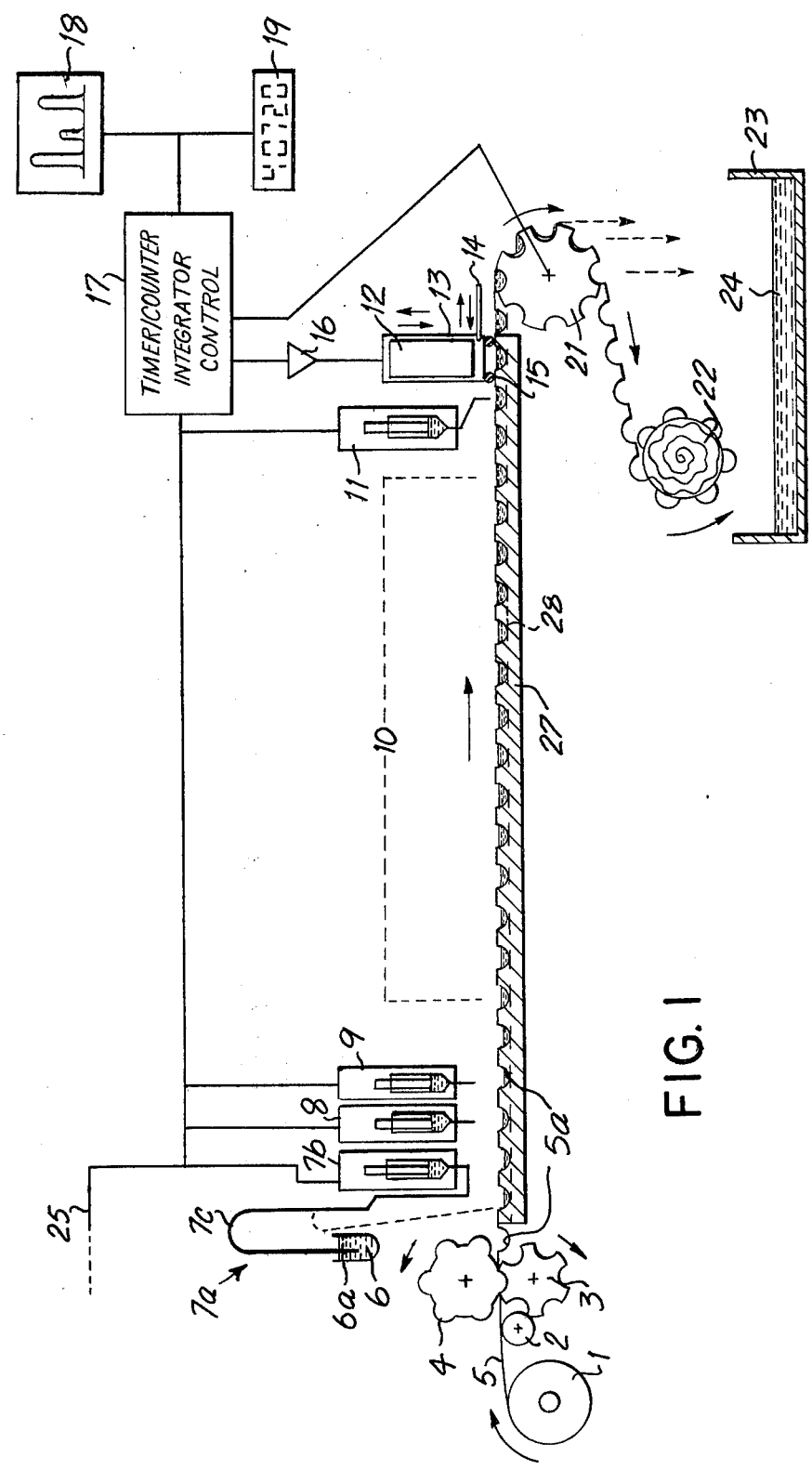
FIG. 1 is a diagrammatic view of the over-all system for measuring the luminescence of discreet samples according to the present invention.

The principles of the present invention are schematically described in FIG. 1. Sample container and sample transport is based on an aluminum or other non-transparent, reflecting tape or foil 5, such as aluminum foil which allows forming of constant shape depressions 5a with a punch in the form of a wheel 4 (male part) that presses the tape against an anvil in the form of a wheel 3 having corresponding depressions (female part). The tape may also be made from a deformable synthetic material, such as polyvinyl chloride. The shape of the depressions or wells for the samples is preferably that of a half sphere, but it may be conical or a slightly cone-shaped cylinder when made with a punch. The diameter of such wells may vary from 2 mm to several centimeters such as 5 cm, depending on the sample type and reagent system or maybe from 1 to 25 mm deep. Small wells are preferable as they save in reagent costs and allow more samples to be contained per unit length of tape. The wells are positioned in the tape in such a way that the distance between the edges of two consecutive wells is a minimum of 1 mm and preferably less than 20 mm. The thickness of the tape may vary widely, but a thickness of from 0.01 to 0.5 mm is preferred.

Two types of sample volumes may be anticipated, one being very small (1–10 $\mu$l) for immunological testing (such as HLA tissue typing) and a more generally applicable sample size between 100 and 500 $\mu$l. However, sample sizes up to several milliliters are possible.

A roll 1 of the non-transparent tape 5 passes over a guiding roller 2 to the counter wheel or anvil 3 with indentations for forming the sample wells 5a in the tape in conjunction with wheel 4 having corresponding protrusions. A sample 6 in a container 6a such as a vial, tube, or cup is delivered via an automatic sample transport unit 7a to wells 5a in the tape 5. Unit 7a includes a diluter 7b and a tube 7c. the end of tube 7c is movable from the position shown in solid lines in which it dips into container 6a to the position shown in dash lines in which it is above a well 5a. Diluter 7b contains a cleaning agent or suitable reagent by means of which the sample from container 6a is displaced from tube 7c into well 5a while at the same time cleaning tube 7c so that it may pick up the next sample without contaminating the same. Details of unit 7a are not described here, since they are well-known in the art. Numerals 8 and 9 designate dispensers for reagents. Each dispenser delivers a measured volume of the respective reagent at the proper force to enable mixing of the sample and reagent. In a region 10 incubation or a chemical reaction may proceed to completion before another reagent (luminescence reagent) is introduced by a dispenser 11. The light intensity emitted by the sample is measured with a light detector 12 that is enclosed in a housing 13 and protected from outside light by a shutter 14 when the housing is lifted up for advancing the tape 5.

When the housing is lowered onto the sample well, an O-ring 15 makes a light-tight seal as shown in FIG. 1. In this position the shutter 14 is moved from the front of the detector 12. Electrical current or pulses from the detector are processed by an amplifier 16 and a timer-counter-integrator-control unit 17. Well-known printed circuit boards, microprocessors or microcomputers may be used as unit 17. The intensity and quantity of the measured substance can be recorded through an analogue output with a recorder or oscilloscope 18, or digitally with a digital panel meter or printer 19.

The control unit 17 synchronizes the stepwise movement of tape 5, deposition of samples in the sample wells 5a by unit 7a, the dispensers 8, 9, and 11 as well as the movement of detector housing 13 and shutter 14. A wheel 21 moves the non-transparent tape 5 forward stepwise in synchronism with wheels 3 and 4. The tape is collected on a roll 22 and the samples drop as waste 24 into a container 23. Power for the entire system is supplied via line 25.

The tape 5 with the sample wells 5a is guided and supported by a metal block 27 (FIG. 3) that has longitudinal grooves 28 having a slightly larger cross section than the sample wells 5a, but having the same shape as the wells. This guiding block allows the forming of a light-tight seal between the light detector 12 and the sample well 5a by the O-ring 15 as well as heating of the samples to a constant temperature during incubation. The O-ring 15 is pressed between the detector housing 13 and the tape 5 which is supported by the grooved block 27.

Figure 2:
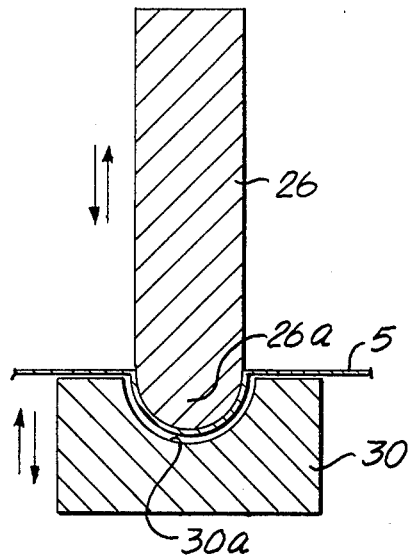
FIG. 2 is a section through a device for making depressions or wells in a tape for the samples.

FIG. 2 shows an alternative device for making sample wells in the non-transparent foil 5. It has a punch 26 with a convex head 26a and an anvil 30 having a concave depression 30a. The punch would replace wheel 4 of the FIG. 1 embodiment and moves up and down in a synchronous manner controlled by the unit 17 controlling the whole system. The head of the punch may be spherical, conical or a slightly conical blunt rod and the anvil part a mirror image of the above to form sample wells of the shape of a half sphere, conical or cylindrical cup, respectively.

Figure 3:
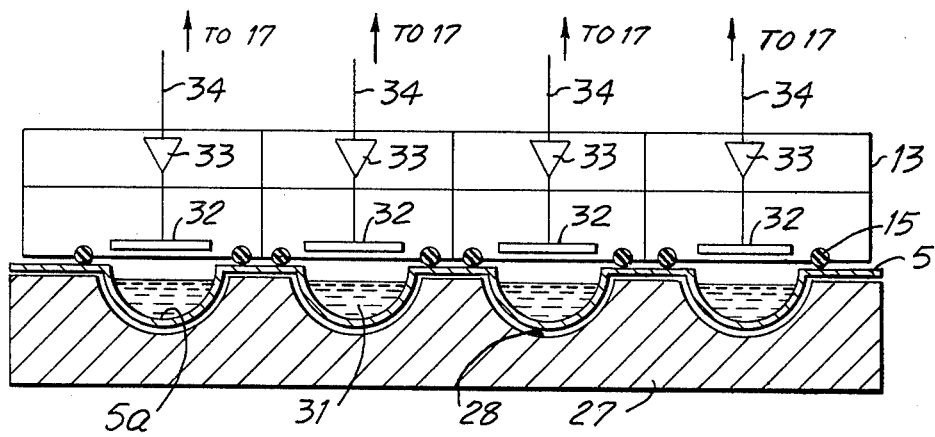
FIG. 3 is a section through a part of a modified system according to FIG. 1, for measuring the luminescence of rows of samples.

FIG. 3 schematically illustrates an example of a multidetector system applied to an aluminum tape 5 and with grooves 28 supporting the sample wells 5a and the tape. The non-transparent tape 5 having the samples 31 in the wells, is supported by metal or plastic block 27 having the grooves 28 slightly wider than the sample wells 5a. In the multidetector system the light intensity of each sample in a row of parallel samples is measured with a separate detector 32. The signal or pulse of each detector is intensified with an amplifier 33 and forwarded to data control and processing control unit 17. The illustration shows solid state (silicon photodiode) detectors 32 enclosed as an array in housing 13. FIG. 3 also illustrates the principle of a multichannel instrument. The tape 5 may have 2 to 20 parallel sample wells 5a and each one of them is measured by a separate light detector 32, which can be either a silicon photodiode or a photomultiplier. The detectors have individual amplifiers 33 and the measured light intensity (as electrical current or pulses) is processed and recorded individually for each detector through individual leads 34.

Figure 4:
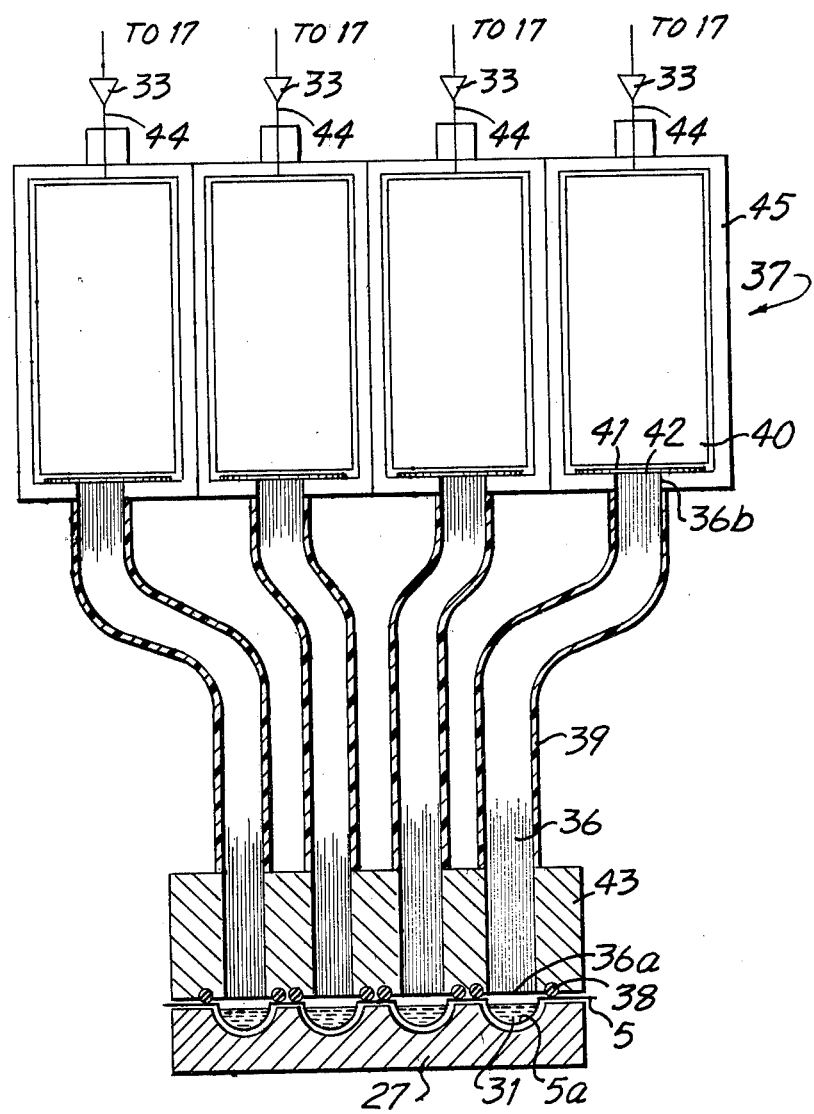
FIG. 4 is a section similar to that of FIG. 3 through an alternative system.

FIG. 4 is a schematic illustration of a multidetector system utilizing optical fibers to conduct light to an array of photomultiplier detectors. Emitted light from samples 31 in the wells 5a of reflecting tape 5 is conducted through bundles of optical fibers 36 to photomultiplier tubes 37. The ends 36a of fibers 36 are isolated from outside light by O-rings 38 which are pressed against the tape that is supported by the grooved block 27. The optical fibers 36 are insulated by a non-transparent sheath 39, and the other ends 36b at a photocathode 41 of a photomultiplier tube 40 are covered with shutters 42, between measurements. This shutter 42 protects the tube 40 from ambient light when the measuring head 43 is lifted up to move the tape 5 to the next row of samples. The shutters are removed from the front of the photocathodes 41 automatically prior to measurement and returned back after the measurement. The electrical current or pulses from each detector are led to an amplifier (not shown) and data processing by individual wires 44. The photomultiplier tubes 40 are enclosed in an array of housings 45.

It is also possible to use a bundle of optical fibers 36 and a single photomultiplier detector 37 to measure a whole row of samples. In this system the fiber bundle will move from one sample position to another until all wells in a row are measured sequentially. After the scanning of one row, the tape 5 will move to place the next row of samples in the measuring position. The bundle of fibers will again move from the first well through all positions on the row to scan all samples. The tape will move and the measuring cycle starts again, etc.

This apparatus can be used to measure quantities of substances or number of viable cells by means of bio- and chemiluminsecent reaction. A specific example of the measurement of somatic cells in milk is given below:

From a milk sample 6 in an automatic sample changer a volume of 10–100 μl is dispensed to a well 5a. As the sample moves below the dispenser 8, 10–500 μl of an extraction reagent is dispensed into the sample. This reagent comprises of 0.02–0.5% aqueous solution of a non-ionic surface active agent of the type of ethoxylated alkylphenol. During the time the sample moves through the incubation section 10 ATP (adenosine tryphosphate) is extracted from the somatic cells in milk (leucocytes) and epitelic cells by the extraction reagent. When the sample moves below the dispenser 11. 10–100 μl of firefly luciferin-luciferase reagent is dispensed into the processed sample. The luciferin-luciferase reagent comprises of 0.01 μg/ml of luciferase enzymes, 10–100 μg/ml luciferin, 0.5–5 mM EDTA, 5–20 mM magnesium salt in a 10–100 mM biochemical buffer (tris, HEPES, MOPS, TES) having a pH between 7 and 8.2, but preferably 7.75.

After the luciferin-luciferase is added to the sample, it produces a light emission proportional to the concentration of ATP and the quantity of somatic cells in the sample. The light intensity is measured when the sample is moved under the detector 12 and converted to the number of somatic cells by means of comparing the sample reading to that of known standards by the control unit 17. The results are displayed either in analogue or digital form at 15 or 19, respectively.

The invention offers several advantages over the manual and the automatic instruments of the prior art. These include simplicity, versatility in sample size and sample processing, high sample output, high measuring efficiency and the possibility to use single and multiple detectors, and the possibility to perform several different analyses in aliquotes of the same sample simultaneously. Conventional, commercially available sample changers can be coupled with this instrument.

The mechanics of the system is simple and inexpensive. Furthermore, the use of such apparatus is economical because there is no need for measuring cuvettes or vials and the consumption of reagents can be reduced considerably compared to that of manual systems by application of small volumes for the sample and reagents. Miniaturizing with this apparatus is possible due to the application of accurate, automatic dispensers and the high measuring sensitivity resulting from optimal optical sample geometry. Small sample size and the simple principle of the apparatus enables a large number of samples to be processed in a small space. The system can be applied to various types of analyses requiring multiple reagent dispensing, time delays and incubation at constant temperatures as well as rapid heating of the sample.

As mentioned above the tape can have either one row of sample wells for measurement of luminescence with a single light detector, or it can have consecutive rows of 2-20 samples or more for simultaneous measurement of the luminescence with a multi-detector array having an equal number of individual detectors as there are samples in one row. The invention allows the processing and measurement of up to 500 samples per hour with a single row and up to several thousands of samples per hour with a multi-detector system. With the multi-detector system it is possible to measure several parameters simultaneously in different aliquotes of the same sample.

We claim:

1. An apparatus for automatically measuring the bio- and chemi-luminescence in a plurality of samples, comprising:
   means for making successive sample wells in a non-transparent, light-reflecting tape, means for transporting the tape along a path, means for delivering a measured volume of a liquid sample into each well at a first location along said path, means for dispensing a measured volume of at least one reagent into said liquid sample in each well in said tape in at least one further location along said path to generate luminescence, light-detector means adjacent said tape along said path and spaced from said dispensing means along said path and adapted to detect light generated in situ from the mixture of the liquid and said at least one reagent in each respective well, said detector means generating a corresponding electrical signal, said detector means engaging the outer periphery of successive wells and provided with resilient means for forming a light tight seal between said detector means and said wells thereby excluding ambient light from entering said detector means during measurement of a sample, shutter means synchronized to exclude ambient light from said detector means during movement of said tape from one of said wells to the next. Means for processing said signal, and control means for synchronizing the operation of said transporting means, said delivering means, dispensing means, said light detector means, and said processing means.

2. An apparatus according to claim 1, wherein said means for making wells includes a wheel and co-operating counter-wheel adapted to make depressions in said tape.

3. An apparatus according claim 1, wherein said means for making wells is a punch for making depressions in said tape.

4. An apparatus according to any one of claims 1 to 3, wherein said means for making wells is adapted to make at least one row of consecutive wells in said tape so that they extend in the direction of movement of said tape.

5. An apparatus according to any one of claims 1 to 3, wherein said means for making wells is adapted to make parallel rows of consecutive wells in said tape, each row extending transverse to the direction of movement of said tape.

6. An apparatus according to claim 5, wherein said tape comprises rows of from 2 to 20 wells extending transverse to the direction of movement of the tape.

7. An apparatus according to claim 6, wherein said light detecting means comprises a plurality of light detectors corresponding in number to the number of rows of wells in said tape.

8. An apparatus according to claim 7, wherein said light detectors are silicon photodiodes.

9. An apparatus according to claim 6, wherein said light detectors are photomultiplier tubes, and wherein optical fibers transmit light from the respective well to the respective tube.

10. An apparatus according to claim 1, wherein said tape is made from synthetic material.

11. An apparatus according to claim 1, wherein the minimum distance between the edges formed by adjacent wells of the same row is approximately 1 mm, and the maximum such distance is 20 mm.

12. An apparatus according to claim 1, wherein said tape and sample wells are guided by a substantially rigid block provided with longitudinal grooves adapted to receive said sample wells and guide the same, and further adapted to support said tape about the wells to cooperate with said resilient means in forming said light tight seal between said detector means and said wells during measurement of a sample.

13. An apparatus according to claim 1, wherein said tape is a metal foil having a thickness of from 0.01 to 0.5 mm.

14. An apparatus according to claim 13, wherein said metal is aluminum.

15. An apparatus according to claim 1, wherein each well has the shape of a half-sphere.

16. An apparatus according to claim 15, wherein the inside diameter of said well is between approximately 2 and 50 mm.

17. An apparatus according to claim 1, wherein said well has the shape of a cone or cone-shaped cylinder.

18. An apparatus according to claim 17, wherein the depth of said well is between approximately 1 and 25 mm.

19. An apparatus according to claim 1, wherein said light detecting means is a single light detector.

20. An apparatus according to claim 19, wherein said light detector is a silicon photodiode.

21. An apparatus according to claim 19, wherein said light detector is a photomultiplier tube.

* * * * *